United States Patent [19]

Förstermann et al.

[11] 4,173,898
[45] Nov. 13, 1979

[54] SYSTEM FOR NONDESTRUCTIVE, ULTRASONIC TESTING OF TEST OBJECTS

[75] Inventors: Ulrich Förstermann, Spröckhovel; Hans-Peter Schäfer; Peter Möller, both of Wuppertal; Dieter Lather, Rheurdt; Karl Ries, Mülheim; Klaus-Uwe Jannsen, Lintorf, all of Fed. Rep. of Germany

[73] Assignee: Mannesmann Aktiengesellschaft, Dusseldorf, Fed. Rep. of Germany

[21] Appl. No.: 816,149

[22] Filed: Jul. 15, 1977

[30] Foreign Application Priority Data

Jul. 16, 1976 [DE] Fed. Rep. of Germany ....... 2632674

[51] Int. Cl.$^2$ .......................................... G01N 29/04
[52] U.S. Cl. ........................................ 73/611; 73/612
[58] Field of Search ................. 73/611, 612, 625, 626, 73/628, 609, 602, 619, 620; 364/507

[56] References Cited

U.S. PATENT DOCUMENTS

| 3,555,889 | 1/1971 | Weighart | 73/612 |
| 3,942,358 | 3/1976 | Pies | 73/611 |

FOREIGN PATENT DOCUMENTS 166160  10/1963  U.S.S.R. .................................. 73/611

OTHER PUBLICATIONS

B.G.W. Yee et al., Computer Automated Ultrasonic Inspection System for Aircraft Forgings, AD775-736, General Dynamics Technical Report AFML TA7-3-194, Oct. 1973, P1-102, P1-48, supplied as pertinent.
Young et al., Digitally Controlled Ultrasonics for Testing Steel on Line, Non-Destructive Testing, Jun. 1976, pp. 131-135.

*Primary Examiner*—James J. Gill
*Attorney, Agent, or Firm*—Smyth, Pavitt, Siegemund, Jones & Martella

[57] ABSTRACT

The system includes a plurality of individually selectable transmitter and receiver channels, a common controller and a common acquisition unit constructed to operate on the basis of parameters which are furnished to the controller and the unit as input signals. Some of the parameters are held in a memory and are withdrawn on the basis of test identification numbers to set up the acquisition unit. The acquisition unit has a transit time counter and two parallel operating looking window generators and several comparator stages, operating under utilization of such parameters. The data as acquired by a test, are accumulated and processed to determine new parameters, if necessary, and feeding them to the memory. The controller conducts the tests on the basis of sequencing the system through a group of test identification numbers, and provides also launch delay and receiving delays on the basis of externally, updatable parameters.

28 Claims, 2 Drawing Figures

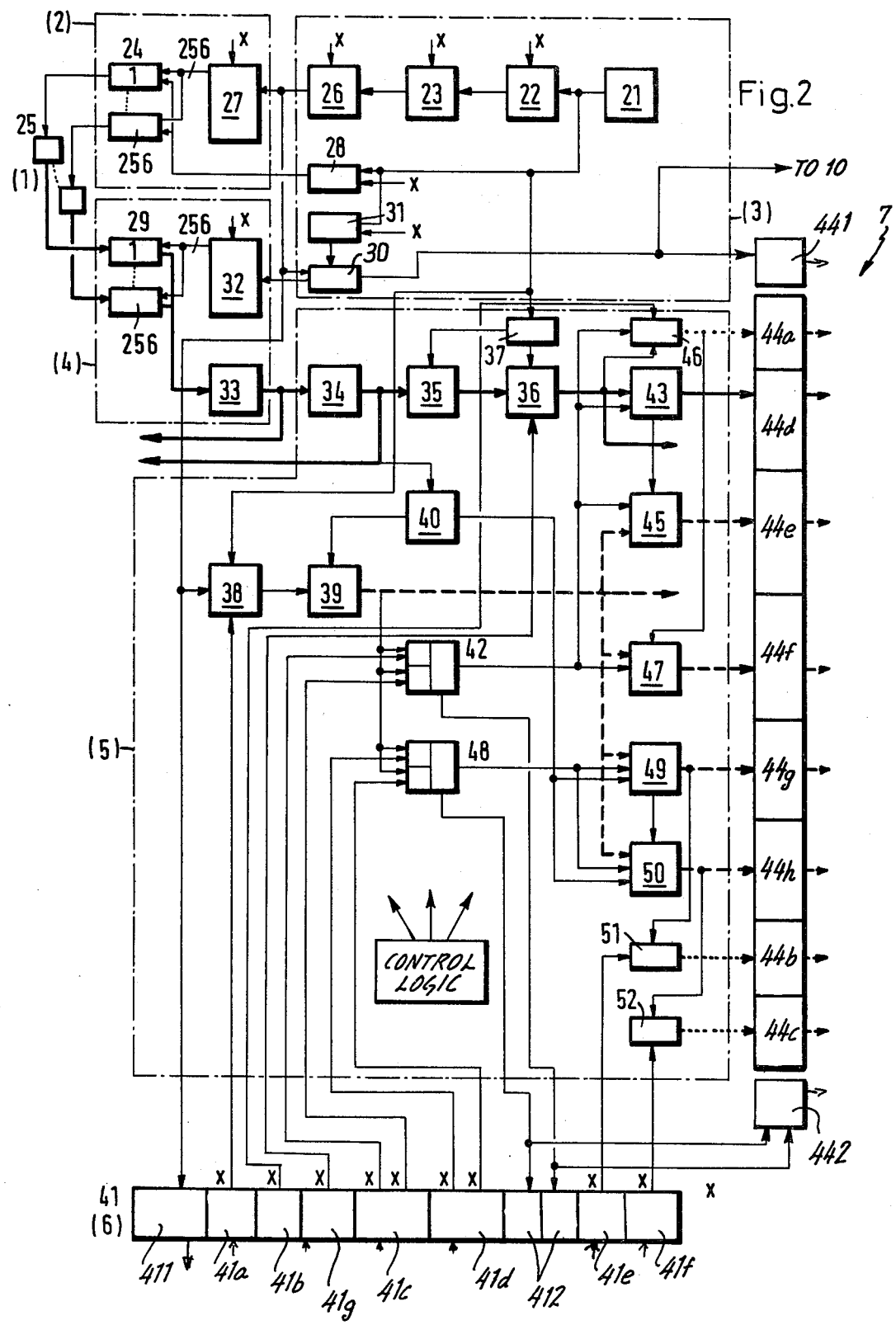

SYSTEM FOR NONDESTRUCTIVE, ULTRASONIC TESTING OF TEST OBJECTS

BACKGROUND OF THE INVENTION

The present invention relates to an electronic system and device which includes means for generating ultrasonic signals as well as means for receiving and processing ultrasonic signals which have interacted in some fashion with a test object and have been received and converted into electrical signals.

Ultrasonic test equipment for the inspection of objects as to flaws and defects are known in a variety of systems and types of equipment. Generally speaking, test equipment of this type includes a signal generator or trigger generator operating a transmitter circuit which in turn drives a transducer producing ultrasonic waves. The same or another transducer is suitably placed, operated and coupled to the test object for receiving ultrasonic signals and converting them into electrical signals. These signals represent some kind of interaction of the ultrasonic test signal with the test object in a particular zone or region thereof. The receiving circuit includes amplification means having a gain that is for example made dependant upon the (expected) signal transit time. The received signal is processed in some fashion whereby particularly so-called looking windows are generated which are enabling and disabling signals to be applied to electrical transmission circuitry to suppress signals from the receiving transducer except for a particular adjustable period of time in which the interaction signal, if at all, is expected to occur. The test equipment of the known variety is also known to include comparators and threshold detectors which respond if particular limits of signal amplitude and/or particular transit times have been exceeded. The tests are conducted in steps, because each individual test inspects only a limited zone or region of the test object. On the other hand, a larger system includes a plurality of subsystems each including means for the transmission and means for the receiving of ultrasonic signals for thoroughly covering the interior of the test object.

The various signals as received and acquired are further processed in order to obtain the desired information on the internal state of the test object. It is inherent that the various tests carried out by different subsystems involve different aspects and do not operate with the same parameters. The timing of a test step; the phase of the transmitted pulse within a test step period; the phase and duration of the looking window or windows; the threshold detection of both signal transit time and amplitudes and other parameters may vary for the different portions of the equipment. These variations are produced usually by appropriately operated adjusting elements. In the case of many such transmission-receiving channels or subsystems, operating in total with k steps and having as far as the equipment hardware is concerned i adjustable membes for the adjustment of the parameters for each test, the number of adjustable components is k times i. It can readily be seen that an extensive test system is encumbered by a large plurality of adjustable elements. More importantly however, the probability of incorrect adjustment as well as the time spent for adjusting increases.

Particular ultrasonic equipment has been constructed for purposes of inspecting tubes, pipes, sheet and plate stock, reactor walls, etc. One has used here computers for the acquisition and evaluation of the measuring data, processing particularly amplitudes, limits, transit times, etc. The known systems, however, were found to be deficient with regard to the adjustment in the test electronics. In other words, the known equipment is characterized by a complete separation of test electronics which operates the transmitting and receiving transducers, and the processing of the data acquired. We found as specifically deficient that the known equipment does not permit the updating of the operating parameters of the test electronic for example, on the basis of the acquired past data. Consider for example equipment currently used for the purposes of testing welding seams. The equipment is designed specifically for automatically testing the entire welding seam of, for example, a long tube or of two sheets, etc. Prior to an automated test run an operator has to acquire empirically information, for example, concerning the periods of time in which certain interaction signals with the test object are expected to arrive. Also, the expected normal, regular amplitudes are empirically ascertained. These initialization runs are carried out, for example, by means of an oscilloscope on which the operator observes the timing and/or amplitude of the various signals. Thereafter he uses that information he personally has acquired in order to adjust the electronics. If the system is an extensive one, a multitude of such adjustments have to be made, and as was outlined above, the probability of erroneous readings and of incorrect adjustments increases with the complexity of the equipment. Generally speaking the operator becomes a part of the system, and if for some reason errors occur a repetition of the test run is required, but again, the operator becomes a critical link as far as the adjusting of the equipment is concerned, etc.

DESCRIPTION OF THE INVENTION

It is an object of the present invention to avoid the deficiencies outlined above and eliminate the above mentioned "human feedback" and to permit the utilization of the acquired test data for purposes of adjusting the operating data of the test electronics.

In accordance with the preferred embodiment of the present invention, it is suggested to provide for a control circuit and data acquisition unit for ultrasonic signals with plural transmission and receive channels, operated in steps and on a cyclically repetition basis, wherein the circuit and unit are operated in timesharing, multiplex fashion as far as the several channels are concerned, and the various test parameters needed are externally programmable. Consequently, external program means cooperate with that control circuit and the acquisition unit to reprogram them from test step to test step. Parameters being the subject of this program control include primarily the timing and duration of looking windows in which the respective ultrasonic receiver signal is inspected as to specific characteristics. Other parameters are limit values for signal transit times and amplitudes. Still other parameters relate to the timing of transmitter pulses and receiver enabling delays modification of the test sequence and of the duration of a test period.

In furtherance of the invention, the acquisition unit is provided with one or several window generators, a time counter and several comparators and other units which are responsive to the occurrence of specific amplitudes. Typically, several different, sequentially occurring and-/or overlapping windows are generated on the basis of parameters which are unique to the test. These parameters and comparison data such as amplitude and time reference signals and other data, are digitally stored in a memory, in addressable locations thereof, to which access is provided by the controller furnishing test identification numbers, which serve as memory addresses. These numbers are provided either by a counting process or via external control. Memory accessing produces a set of parameters to be used in the current test. The test includes the appropriate launching of an ultrasonic signal which is received after interaction with the test object.

The test identification number serves also as appropriate enabling and selecting signal for a transmitter channel and a receiver channel. This includes also the selection of a transducer to serve as transmitter or as receiver or both but during different phases of a test. The received ultrasonic signal (being converted into an electrical signal) is digitized and processed to determine, e.g., value and time of occurrence of a maximum amplitude in specified (programmed) windows; the occurrence of the onset of specific echos (also within programmed windows); whether or not specific signals exceeded programmed amplitudes or times of occurrence etc. The acquired information being, in the essence, flags, time count numbers, and digitized amplitudes, are accummulated in a buffer as acquired, and under the test identification number to be used further as required. However, in furtherance of the invention, a computing facility processes these data to determine whether the test parameters for the test under that ID-number are better updated, and the updated parameters replace those in memory. The generation of sequential windows is accompanied by tracking-through-counting the windows as generated, and the result of that counting is used as window address to distinguish among the several numbers identifying windows to be used under the same test identification number. Also, these window addresses are used in association with that number to distinguish among the several process results and data. In that capacity they serve as output buffer addresses.

It can thus be seen that the test electronics comprising essentially a controller-timer-sequencer, transmitter and receiver channels with select electronics, and the acquisition circuit which identifies signal portions on the basis of specific windows and under utilization of reference data as to amplitudes and transit times, is constructed from elements which, on one hand, are shared by all tests involving different, selected channels, but each is provided to receive preset numbers as test-specific operating parameters. These numbers are furnished externally from a source for parameters, whereby at least in some instants, these parameters are automatically loaded into the test electronics in the beginning of a particular test under operation of a test identification number. There may be a plurality of such sources, at least one of them, being a memory whose content (as to parameters) is updated on the basis of the test results themselves, so that an integrated, closed loop type parameter source and update system is established. Another source may be an operators console; still another source may be an external, automated source whose data are not updated within a closed loop operation. A further source may be a processor, external to the acquisition unit and the controller, which controls the sequence of the tests and furnishes the necessary selection number, possibly as an update or intervention to regular sequence counting, and also the parameters that determine launch time and beginning of response receiving by the selected receiver channel.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is a more detailed block diagram of several major components of the diagram of FIG. 1.

Proceeding now to the detailed description of the drawings, FIG. 1 illustrates an ultrasonic test apparatus operating on the basis of time multiplexing for testing an object in plural cycles, each cycle being established by a plurality of test steps. A transmitter circuit 2 includes the individual transmitter channels for controlling (triggering) a plurality of transducer heads 1. Each head as connected is to include either an ultrasonic transmitter or a transducer that can be operated in the transmit mode.

Figure 1:
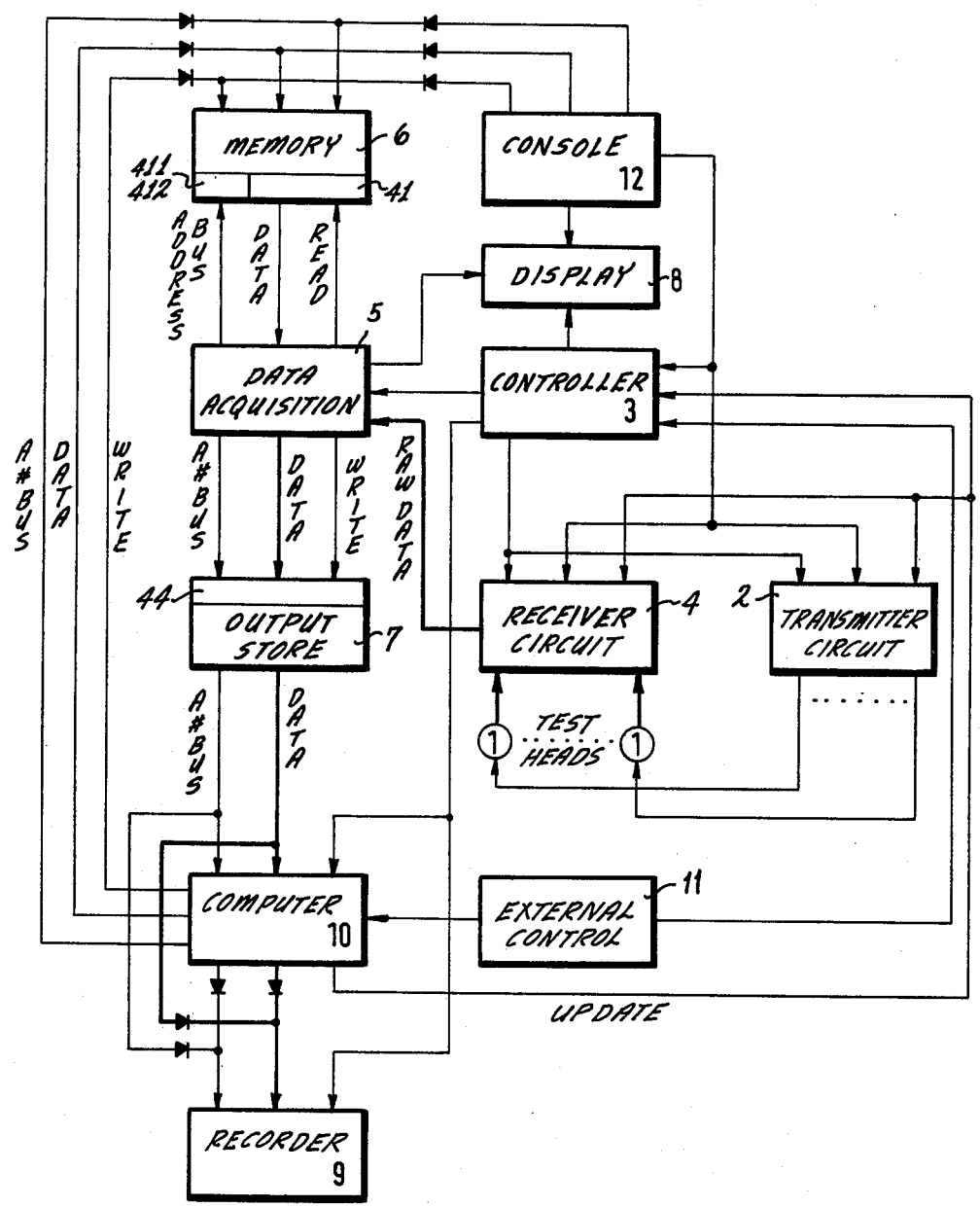
FIG. 1 is a block diagram for a system in accordance with the preferred embodiment.

The transmitter channels in unit 2 are selected individually in accordance with a particular test program and test step sequence, and they are operated specifically as to launching or on ultransonic signal by timed control and trigger signals derived from a controller 3. The launch delay is a programable parameter. The controller 3, as will be shown below, determines the test step sequence which includes a sequence of enabling the various transducers. However, that sequence can be modified externally (as regards the controller). The respective transmitter (1) operated in that fashion issues an ultrasonic pulse or burst, one per test step. The selection, therefore, includes also the mode control for any of the transducers whether to be operated by a transmitter channel.

Controller 3 operates also a receiver unit 4 having a plurality of receiver channels which are connected to the receiving transducers of the heads 1 or to the transducer of a head as operated in the receiving mode. The operation of receiver circuit 4 by controller 3 is also carried out pursuant to a test program (test step sequence) and involves the timing (gating) as well as the selection of the particular receiver channels. The selector, therefore, includes also a mode control as to whether to operate a transducer as receiver. The enabling is also timed (delayed) in accordance with a programable parameter.

The receiver unit 4 includes appropriate amplifiers, and the amplified analog signals are fed to an acquisition unit 5 which includes, among other elements, a transmit time counter (infra). Unit 5 includes also analog-to-digital conversion means as well as associating circuitry which associates the digitized signals as received from an ultrasonic receiver channel with time counts (i.e., with periods defined by pulse counting) to meter the time between launching of an ultrasonic signal in the selected transmitter channel and the responses as received subsequently by the selected receiver channel.

An input store (read/write memory) 6 stores data representing operating and control parameters for the acquisition unit 5 including gating periods and their phases defining particular looking windows following the launching of the ultrasonic signal. Order such parameters are amplitude and transit time limits values as well as predetermined delays to be included in (subtracted from) the metering-through-counting of signal transit times.

The addresses, for access to the several memory locations, are provided by the acquisition unit 5, but are ultimately derived from the controller 3 as test identification numbers. The address bus from 5 to 6 will however include additional addressing signals as will become apparent below.

The acquisition unit 5 operates in accordance with a sequence of test steps, based on a sequence of test identifications numbers, and accesses the locations in memory 6 holding the parameters associated with the current test step as identified by the test identification number. Since this is a memory read operation, a read signal line leads from unit 5 to the memory to institute a read cycle. Otherwise devices 5 and 6 are interconnected by an address bus and a data bus.

The unit 5 includes control and processing facilities in order to meter relevant transit times and to associate digitized signal amplitudes and transit times with the parameters extracted from memory 6. Most importantly, unit 5 generates looking windows to restrict recognition of specific characteristics in the ultrasonic signals as received to limited periods of time for purposes of suppressing noise and for purposes of identifying specific signal portions as having resulted from specific interaction of the ultrasonic signal with the test object and its boundaries.

As a consequence, unit 5 may produce and extract from the raw data as received by the ultrasonic receivers the following measuring values as process data: (a) the maximum detected amplitude within individual looking windows; (b) the transit time thereof; (c) signals representing that particular amplitude limits or thresholds have been exceeded; (d) the transit times associated therewith; (e) signals representing the transit time of particular echoes such as the echo of the ultrasonic signal at the entrance interface between coupler medium and test object; (f) signals representing the thickness of the test object; (g) signals representing the fact that certain transit time limits were exceeded.

These signals are fed by unit 5 to an output store, for resultant data and buffer 7 (possibly being an addressable memory), in association with the test identification number as well as window identification numbers. This number may also serve as an address here. In addition to the data and address busses a write-command line leads from unit 5 to store 7. Concurrently thereto the raw analog ultrasonic signals as received, the (raw) digitized ultrasonic signal amplitudes, detected transit times and control signals are displayed for example on an oscilloscope or oscillograph 8. By way of example, the data signal train that appears in the receiver output line or data bus from 4 to 5 may be displayed beginning with the time of launching of the particular ultrasonic transmitter pulse. The other parameters displayed may be some of those fed to store 7.

The content of output buffer 7 is either fed directly to a recorder 9 or is fed first to a computer 10 for being processed therein together with parameters taken from an external controller 11. These parameters are, for example, geometric coordinates identifying the zone or region of the test object that was inspected by the particular test step. After having been so processed, the data are recorded in 9. Both, computer 10 and recorder 9 may be operated in synchronism with clocking signals generated in controller 3. Moreover, the controller 3 furnishes to the computer 10 the test identification numbers.

The computer 10 executes also a program according to which new gating periods, and/or amplitude limits are computed to replace those previously used. Also, the test program and step sequence may be altered or modified which may require the computing of new control data, addresses and test identifying numbers, etc. Specifically, each location or set of locations accessed in memory 6 as per a test identification number holds the test parameters needed for the data acquisition of a particular test within the sequence of tests. These parameters are, possibly, recalculated by the computer 10 and returned to memory 6 as updated versions of the parameters to be used either in a subsequent test of like identification or as a repeat.

In addition the computer 10 may command a repeat of the test just finished under utilization of the new data, in which case computer 10 will return the test identification number to the controller 3 via the (or a portion of the) update bus from 10 to 3, so that the next test will not be the one which will normally follow a completed test step. Generally speaking then, computer 10 may completely alter the sequence of tests, and determine that sequence by furnishing test identification numbers to the controller.

An example of an update program for test and control parameters is, for example, disclosed in patent application of common assignee, Ser. No. 775,159, filed Mar. 7, 1977.

The external controller 11 may, in the alternative, take over the control over the sequence of tests, in which case controller 11 will intervene in the operation of computer 10. Device 11 may be operated in dependence upon the relative advance between test heads and test objects, requiring in specific cases a deviation from normal operation under direct control of the computer 10.

Generally speaking, computer 10 either determines or receives the test identification numbers and may draw on its own memory (or a separate portion of 6) to update the operating parameters used by controller 3 and units 2 and 4 in the conduction of the test, which involves the transmitter and receiver selections and the timing of the test signal launch as well as the beginning of enabling the selected receiver. These parameters may also be updated from test to test, but now by the computer 10 feeding those parameters, directly to devices 2, 3, and 4, just prior to the beginning of a test and as an initialization procedure to set up the subsystem 2, 4 for the launching of an ultrasonic test signal and the beginning of the desired receiving of the return response following interaction with the test object.

From a different point of view, computer 10 is designed to control the data content of memory 6 as far as the parameters needed in the acquisition process is concerned. These data are then taken from memory by acquisition unit 5 when needed. The operating parameters for units 2, 3, and 4 may be stored separately in computer 10, or in memory 6, but they are fed to the subsystem 2, 3, 4 right in the beginning of a test, as soon as a new test identification number has been issued. The control and operating program for the computer 10 itself may be resident in the facility itself or also in memory 6.

Alternatively, computer 10 may receive such parameters externally from device 11 while other parameters (not held in memory 6), including test identification numbers, may be provided by the control 11 to the controller 3, and the circuits 2 and 4. The test identification number will then be used by the computer 10 to load the memory 6 with the parameters provided by control 11 to computer 10 for that purpose.

Reference numeral 12 refers to the operator's console for inputting data that may modify the test program and its execution. These modified data will also be fed into the store 6, for example, under manually selected addresses (or through punched cards). This input operation may be carried out in parallel to regular proper execution, but should be used sparingly. Generally, all data in subsystem 2, 3, 4, and 6 as they may be updated through operation of the computer 10, may be updated manually through the console.

Programming of the system as per FIG. 1 (and 2) is carried out digitally because reproducibility of the tests is better ensured than in the case of analog programming and adjusting. Particularly temperature dependant deviations in the operating parameters are avoided.

The test of the object inspected is carried out in cyclically repeated sequences. That is to say, the controller 3 activates a sequence of transmitter and receiver channels through issue of test identification numbers. After having completed such a cycle, the computer 10 may detect the end of a sequence or the controller 3 may command a relative advance between test equipment and test object, whereupon another sequence is begun, preferably under utilization of updated parameters.

After having described the inventive system in general terms, we now turn to FIG. 2 showing many of the units (particularly units 2, 3, 4, 5, 6, and 7) in greater detail. The controller 3 includes a master oscillator 21 to which is connected a frequency divider 22, which, in turn, feeds a clock signal to a switch 23, which either passes that internal clock signal or receives and passes an external clock. Use of either is arbitrarily selectible. The external clock may, for example, be derived from the production process of the test object as it passes through the test stand, combined with a clock from processor 10, indicating that evaluation of the previous test is completed. Both external clocks have to appear before an output signal is produced by the circuit 23.

The frequency divider ratio (if the controller clock is, in fact, used for test sequencing) is also programmable externally. For example, device 22 may be a counter which recycles when the count number equals the dividing ratio. The count number may be subject to a change by use of a comparator and a register into which a programmed number is set, and when the counter reaches that number, the comparator responds and resets the counter to start a new cycle. The divider ratio and number of counted pulses is an important parameter because it determines the length of the period of time alotted to each test. The output of 22/23, therefore, is a test step sequence clock.

The test step clock signal is used to operate a test step counter 26. It may be assumed, that a test cycle may involve 256 different test steps so that 26 is an eight bit binary counter. However, the counter is presettable, so that it may be advanced or returned to a lower number at will. Generally speaking, device 26 furnishes the test identification number to be used throughout the system. That number can be updated through a regular counting process, but the content of device 26 can be replaced, e.g. as was outlined above, by a number furnished by the computer 10. If a repeat of the same test is desired counter 26 may simply be held to its current count state on the next step sequence clock pulse which, in effect, is suppressed in that case. The "x" on these units is to denote possible external sources for update or replacement originating with 10, 11 or 12.

The content of counter 26 is fed from unit 3 to unit 2 and particularly to a decoder 27 having an input register and as many output lines as there are different test and transducer-transmitter channels to be activated. These channels are collectively designated by numeral 24 and additionally identified by numbers 0 to 255. The channels or transmitter circuits 24 are individually enabled (and selected therewith) by the decoded test step number from counter 26. In addition, all transmitter channels 24 receive a trigger signal from a delay stage 28 (in controller 3), to be effective in the selected transmitter channel. The delay is subject to programming and can be selected for each test step by computer 10.

Delay involves, basically, a period between updating of the test number state 26 and the actual commencement of the test by launching an ultrasonic signal into the test object. One aspect of the necessary delay is that this test identification number has to be fed to different parts of the system whereby particularly specific parameters needed for that test are withdrawn from memory 6 and set into a register 41 as will be described more fully below. The length of the delay could be one of the parameters which are extracted from the memory location which is associated with the identified test or, better, a modification of that number could be so provided, but such modification is a rare occasion so that it is not necessary to alot storage space to each test for that purpose.

The trigger delay is produced by device 28 by a counting process, counting clock pulses from 27 up to a preset number. This way, the timing of each trigger signal that is effective in any selected transmitter channel is delayed from the time stage 26 holds a new test identification number. Counter 28 is reset on each test stepping signal from 23. The trigger signal is, of course, responsible for the launching of an ultrasonic signal by the transducer 1 that is controlled by the particular selected transmitter circuit and channel 24. The transmitter channels 24 are, basically, selectible and triggered driver stages for the respective ultrasonic transmitter they control. They may however individually be replaced by, or function-share a programable function generator which provides a particular signal or a sequence of signals per test, one of which signals may serve as pilot signal of specific amplitude and to be specifically monitored as to specific interaction with the test object such that the system is checked and self tested. The pilot signal must produce a specific response in terms of amplitude and transit time, to be received separately by a pilot receiver under conditions which permit the conclusion of correct or incorrect operation of the system as such. These pilot signals issue and are received under the current test identification number and may be associated and compared with suitable reference signals.

The receiver unit 4 has a corresponding plurality of individual receiver channels 29 which are individually enabled and selected by a decoder 32. The decoder 32 receives the content of a register 30 as an input for purposes of decoding. Normally, that content is the count and test identification number received from counter 26. The register 30 either receives that number or applies it to decoder 32 in accordance with a delayed clock, the delay being produced by a programable delay stage 31, being also a counter which is presettable and counts clock pulses form the master clock 21. The delay as counted in this fashion may also be one of the parameters which are furnished by the computer 10 for specific use in the test as currently identified. Delay counter 31 is reset also when the test identification number is changed. Regardless whether the delay as per counter 31 is used for delayed gating of the test identification number into register 30, or whether the content of register 30 is delayedly applied to decoder 32, the decoder enables and selects a particular receiver channel circuit 29, with a programmed delay as compared with the enabling of the transmitter channel participating in the same test (as identified by the test count number). This selection may include the specific operating mode for a transducer 1 in that the same transducer which operated as transmitter either in the same test or in another test, is now enabled to operate as receiving transducer in that the signal receiving circuitry connected to it is now enabled. It can thus be seen that decoders 27 and 32 as such are instrumental in selecting the desired mode of operation for any transducer, and the programmable units 28 and 31 furnish the timing of the specific operation as selected; delay counter 28 times the actual transmission of an ultrasonic wave, and delay counter 31 times the subsequent beginning of the receiving operation of that test.

It should be mentioned that the decoders 27 and 32 may themselves be programable in the sense that the association between test identification number and transmitter and/or receiver channels may be changed through external commands. These commands may for example, involve index numbers which are added to the numbers applied by 26 and 30 to decoders 27 and 32 respectively. This may be of particular interest in the case of parallel operations of several transmitters and-/or receivers. The decoder continuum may be larger than 256 whereby the additional numbers when effective are decoded as multiple gating and enabling signals, enabling several transmitter and/or receiver channels simultaneously. Such simultaneous operation could, however, be included already in the regular decoder operation.

The receiver channels 29 may be connected in groups to different principle or main amplifiers 33 (each channel 29 will include its own preamplifier). Different amplifiers 33 are necessary if the signal level, in spite of preamplification, is still materially different among the multitudes of channels. Most importantly, however, one may need different amplification characteristics. Thus, some channels may require linear, other logarithmic, others still different non-linear amplification characteristics. Amplifiers 33 are designed accordingly to meet these different demands. The use of a logarithmic hf amplifier is of particular interest because without change in gain one may amplify ultrasonic signals over a dynamic range of about 80 dB. This renders impossible arbitrary manipulation of the measuring signals.

Each of the amplifiers 33 feeds an impedance matching unit 34 which may include also rectification. The junction between an amplifier 33 and a unit 34 is connected to an instrument which indicates the respective high frequency amplitude. The output of rectifier 34 is also connected to an instrument to indicate the rectified signal amplitude. In FIG. 1 this was indicated by connections to display unit 8.

The rectifier 34 pertains already to the acquisition unit 5 and feeds a sample-and-hold circuit 35 which is clocked from master clock 21 via a control stage 37. The clock 21, basically, represents the resolution of metering time in the circuit as will become apparent shortly. That resolution is not necessarily necessary for the discrimination of amplitude values. Therefore, stage 37 may be provided to reduce the sample-and-hold rate as compared with the clock rate.

The circuit 35 serves as input device for a digitizer 36 which is timed in synchronism with the S+H circuit 35, and with a slight delay to allow for signal settling. It can thus be seen, that circuit 36 provides a stream of digitized amplitudes, which are indiscriminate as to occurance and test; it is a stream of raw digital data. These data are now to be associated with looking windows to permit ready distinction of specific signal components. The digitized ultrasonic measuring signals may be reconverted into an analog signal to be displayed on an oscilloscope.

Acquisition unit 5 includes a transit time counter 39, which is the basic time-metering-through-counting unit of the system. Counter 39 counts clock pulses from master clock 21, but begins counting only after a particular delay has elapsed. This delay is metered by a presettable counter 38 which receives the clock pulses from master clock 21 and blocks these clock pulses from counter 39 until the preset count state has been reached. Thereafter, the clock pulses are permitted to reach counter 39; following this programmed delay, counter 39 begins counting clock pulses, whereby this particular delay has a specific, well defined relation to the time of launching the ultrasonic pulse or pulses by the transmitter used in the current test.

Alternatively, counter 39 can be started in response to a comparator output 40 which receives, as a first input, the rectified analog signal train from the receiver circuit 4, and compares that signal with a second input stored or adjusted in the comparator 40 as a particular threshold input. That second input is a particular limit, and as soon as the raw analog signal exceeds that limit, counter 39 is started. This mode of operation is advisable only if in furtherance of the processing a particular signal timed relation to the launching time is not needed, or acquired otherwise.

The acquisition unit 5 includes an input register 41, which could also be the output register or buffer of memory 6. This register 41 receives all the relevant parameters which acquisition unit 5 needs for the acquisition of measuring data pertaining to one test and step. Reference numeral 411 refers to an address register which may pertain to memory 6 or to acquisition unit 5 which controls the access to a particular group of locations in the memory associated with a particular test. Accordingly, register 411 receives the test identification number of stage 26 of controller 3 in timed control by operation of the acquisition unit 5, conceivably immediately following establishing of a new test identification number in stage 26. However, in the alternative, the address for register 411 may be taken from register 30, because evaluation of received data will not take place until the respective receiver channel has actually been enabled and selected. This means that there may well be an overlap between the sequence of test identification numbers as per counter 26, and the sequence of numbers as sequentially set into and held in register 30. Such overlap may speed up the operation. In either case, register 411 controls the access to memory 6 on the basis of the current test identification number and causes register 41 to be filled with the content of that accessed location. Register 41 receives a plurality of different data and control bits held in one particular memory location, but being organized in different fields identified as 41a through 41g, as well as an index or "window" address field 412.

The field 41a contains bits defining the transit time delay for presetting counter 38. Field 41b contains the value for a first amplitude limit. Fields 41c and 41d each contain two numbers which are numbers used for metering gating and looking window periods. Fields 41e and 41f contain numbers defining certain limits for metered periods as will be explained more fully below. Field 41g contains a corrective parameter for the digitizing process.

Field 412 is actually a pair of index registers which contain two numbers which, when concatenated to the test identification number and address held in register 411, identify additional memory locations which contain additional parameters needed for the acquisition; all information needed during a test is not needed initially. Conveniently, it may be assumed that field 412 contains all zeros when initially set. In reality this field may not receive any information from the memory but may be set to zero in the beginning of a test period. Later, this field will receive non-zero bits to access additional memory locations containing additional parameters that are needed in the acquisition process of a test.

It should be noted that memory 6 may be constructed with a higher resolution address continuum than presented by the test identification number used as address and furnished to the memory by address register 411; registers 412 may always furnish low order address bits which are automatically all zeroes in the beginning of each test cycle, but are updated later through window counting. Alternatively, all information may be extracted by memory access on the basis of the address held in register 411, and multiple numbers for the windows (and others as will be described shortly) are all extracted from memory at once and put into a registers stack, a scratch memory or the like. The fields 412 as updated are used as stack pointers to access these registers individually and fill fields 41b, c, and d. It can thus be seen, that any number of windows can be sequentially generated in that fashion within the resolution of the system.

Reference numeral 44 refers to an output register of acquisition unit 5, which may however be an input register for the buffer 7. This register 44 has also a number of fields receiving from unit 5 a number of different digital data that have resulted from the acquisition process. Moreover, certain fields or portions of register 44 serve as input registers for a plurality of push down stack buffers which receive sets of data all pertaining to the same test but to different phases (windows) in the acquisition process of data pertaining to one test under the same ID-number.

The fields 44a, b, c are flags indicating whether or not certain limits have been exceeded. A more sophisticated version may include registers which hold also digital, quantitative information on the particular excess condition if they occurred. Stage 44d will receive the acquired value for the maximum amplitude per window. Stage 44e receives the companion values (time counts) for the transit time of these amplitude peaks. Stage 44f receives a time count signal indicating the instant the measuring signal exceeded a particular threshold level. The stages 44d, 44e, 44f are also the input buffer stages of push down buffer stacks designed to sequentially receive the particular data as pertaining to and acquired during different sequential looking windows and gating periods of the same test.

Stage 44g receives the transit time of a first echo, for example the echo produced when the ultrasonic test signal reached the front boundary of the test object, while a portion of that signal proceeds into the test object. Stage 44h receives a value for the thickness of the test object in the test region. All these data are fed to the computer 10 for further processing.

Reference numeral 441 refers to a portion of buffer 7 which could also be regarded a stage of register 44 and which receives from the controller 3 (possibly via the acquisition unit 5, the diagram of FIG. 1 has been drawn that way) the current test identification number as provided by the stage 26. Reference numeral 442 refers to a portion of buffer 7 which could also be regarded as a twin register and which receives the index numbers used for memory accessing via the sequential updating of field 412. The registers 442 can actually be regarded as a stack pointer providing tags identifying occupied stages in the push-down stacks of device 44, because the several tests may use different numbers of windows in the acquisition process.

We now proceed to the details of the acquisition process. The unit 5 includes two units 42 and 48 which meter looking periods, and keep track of the number of windows as needed and used during the particular test. Unit 42 includes two comparators coupled to the field 41c of register 41 to monitor the current values for the beginning and end of a first window in terms of time as metered by counting of clock pulses.

In other words, the field 41c includes a low number and a relatively high number; these two numbers of field 41c are compared with the running, updated numbers as furnished by counter 39. When that counter has reached the low number, a flip-flop in unit 42 is set marking the beginning of a gating-on period or looking window. The flip-flop is reset when counter 39 reaches the second number. This gating signal as provided by the set state of the flip-flop is used in a manner to be described shortly. Presently, the operation of unit 42 is to be described further.

As the window is closed, unit 42 increments an internal counter setting it, for example, from an initial state of 0 to a state of 1. This window count number is used as index to be added to one of the two index registers 412, to access another location in memory 6 (still under the same test address as held in register 411) or to draw on the buffer stage of 41, under field 41c holding a different pair of window gating numbers, which will now appear in field 41c. In addition, the window count from unit 42 is set into one of the dual registers 442 to keep track of the window count from 42, as far as the output of acquisition unit 5 is concerned, whereby particularly the push-down stack register portions as per fields 44a to f are kept track of to permit sequential storage of the sequentially provided acquired test data associated with windows from unit 42.

The second, newly arrived pair of numbers in field 41c defines a second window, being later in time than the first one because counter 39 continues to run, and we are still in the same test step period. Following the generation of that window, the window counter in unit 42 is again incremented by 1 and one field in register 412 is updated again to call on the data for the next window, if any.

The gating signals thus produced are used in a number of different ways. Unit 42 is provided to generate amplitude looking windows, i.e., it meters discrete periods during which particular amplitudes are to occur (or not to occur, as the specific case may be). The gating signals are applied to a circuit 43 which receives the stream of digitized amplitude signals. These signals may be applied at the clock and time counting rate, possibly as reduced by stage 37.

Circuit 43 is a peak detector which operates on the basis of an algorithm according to which, e.g. the first sampled and digitized amplitude value in a gating-on and window period is stored; the next multi-digit measuring signal is compared therewith and if larger the stored value is dumped and replaced by that large one, etc. At the end of the window period register 43 holds the peak signal value as it occurred in that period. Concurrently to the foregoing, a second register 45 is enabled receiving in addition the time count numbers from counter 39. This count number represents a transit time in each instance which can be associated with the amplitude value then furnished by digitizer 36.

Stage 43 signals to register 45 whenever the content in stage 43 is updated (because the amplitude value furnished is higher than any preceding one during the current window period). That signal is used to gate the current time count into the register 45, replacing any number therein which was previously stored. Thus, at the end of the window, register 45 holds a transit time count for the peak amplitude in that window. These two values are set into the stages 44d and 44e.

As stated, each of the stages 44d, e has multiple substages constructed e.g. in as a push down stack. In the general case, there is more than one window period during a test step, so that plural maximum amplitudes and plural associated transit time count numbers are acquired and stored sequentially in the stacks. The identification of stack stages by the content of registers 442 was already discussed.

The gating signals and looking windows as generated by stage or unit 42 are used in still another acquisition process. Each window (as identified by a window count on the address) is also associated with a pair of amplitude limits, set into stage 41b on initial test step accessing and updated with sequential indices as per window count and tracking by unit 42. These amplitudes are fed, just prior to the beginning of each window, to a comparator 46 which compares each digitized amplitude value from digitizer 36 with these limit or threshold values. As soon as either of these values is exceeded, a flag is set in stage 44a permitting the setting (or not setting) of two flags accordingly. Concurrently with the setting of the respective flag one of two registers 47 is enabled to store the time count from counter 39, marking the instant in which the signal exceeded the respective threshold or limit.

Units 46 and 47 are, of course, also enabled by each window and gating signal from unit 42. The content of register 47 is transferred to stage or field 44f in register 44, being also a push down set of registers. At the end of each window, stages 43, and 45 through 47 are cleared, following the transfer of their contents to the appropriate stages in register 44, and the next clock pulse may be used to push down each stack by one position.

The unit 48 is constructed similarly to unit 42. Unit 48 meters also window periods and keeps track of the number of windows generated. These windows are generated quite independently from the generation of windows by unit 42, the reason being that the windows may overlap, while on the other hand, different items of information are looked for in the several windows and different criterion are applied. For reasons of noise suppression each looking period should be kept as short as possible, and whenever a longer period can be divided into several shorter ones, one will do so rather than generate a large window. The windows generated by unit 48 are specifically designed to look for specific transit times and to isolate and identify specific signals.

Unit 48 takes the count numbers defining beginning and end of the respective windows from the field 41d of register 41. That field is updated following completion of each window by index counting performed in updating of the second window count number in registers 412. Unit 48 receives, of course, also the running time count from counter 39 for comparing that count with the window beginning and window end numbers of the current content of field 41d.

It will be recalled that comparator 40 is an on-line threshold detector, monitoring continuously raw analog signals as fed into acquisition unit 5. Comparator 40 is shown with two outputs which may change signal level states on different adjusted thresholds, one may be used as an alternative input to start time counter 39, and another output (produced for a higher threshold level) as a trigger signal for stages 49 and 50. The gating window signal as generated by unit 48 as well as the window count state are applied to register 49 as a gating signal. Register 49 includes an input decoder circuit to accept the window gate only on the first window. A third input for register 49 is the time count from 39. Thus, register 49 receives, during the first window, a time count number occuring the instant threshold detector 40 detects the onset of an ultrasonic signal in that window. This way the time of the echo is determined, resulting for example, from a reflection of the ultrasonic signal at the coupler fluid-test object interface.

Another typical echo that is being produced is the so-called rear wall echo. On the basis of initialization one will know approximately when that echo occurs and accordingly another pair of numbers is set into field 41d following the first window, and a second window in which that rear wall echo is to occur, is generated by unit 48. The resulting gating signal together with the window count is supplied to a register 50.

The time of occurrence of that rear wall echo is determined again on the basis of the ultrasonic signal exceeding the threshold of device 40 and will be gated during that window period (if occurring) into the register 50. Processing facilities such as an ALU and control logic in unit 5 will subtract the contents of register 50 and 49 from each other to arrive at a number that actually represents the thickness of the test object. The resulting number is returned to register 50 (possibly serving as an accumulator in this arithmetic operation). Following the end of that window, the content of registers 49 (transit time of first echo) and 50 (wall thickness) are set into the fields 44g and 44h of register 44.

Unit 48 operates two additional devices, 51 and 52. Fields 41e and 41f contain two numbers which represent transit time limits. The first number in field 41e is a limit for the transit time of the first echo as acquired by operation of and in regular 49. Hence, the content of register 49 is compared with the content of field 41e by the comparator 51. If the acquired transit time exceeds the programmed limit, the flag 44b is set (or the excess is acquired as a digital number).

Analogously, the limit number in field 41f is a limit value for the test object's thickness (represented of course in transit time counting units). The comparator 52 compares that number with the content of register 50 and sets a flag in fields 44c if this limit is exceeded.

This completes the description of the particular information being acquired during each test, except that the running output of transit time counter 39 is also an output, to be fed to the device (computer 10) which uses the time count number as a reference for further processing.

Field 41a in device 41 has not yet been described. The number held therein defines the particular delay from which transit time counter 39 is to being counting. Thus, this particular field presents the counter 38 right in the beginning of each test.

Field 41g holds a number which will be added to the running sequence of digitized ultrasonic signals to obtain a correction. Such a correction may be needed because the individual receiver channels each receive ultrasonic vibrations under different circumstances and conditions. This is particularly so if, in fact, a single main amplifier is used for all channels.

The control logic of the acquisition unit 5 may be a microgrammed, microprocessor operating basically for register-to-register transfer to obtain proper sequence of operation of the various components in the unit 5. This operation includes also the generation of read and access request signals to memory 6 as well as signals to computer 10, e.g., that the test is completed and all data have been accumulated in buffer 7. Also, all of the various registers and contents in the unit 5 may be reset to zero.

The invention is not limited to the embodiments described above but all changes and modifications thereof not constituting departures from the spirit and scope of the invention are intended to be included.

We claim:

1. In a system for inspecting test objects by means of ultrasonics, having a plurality of individually enablable and triggerable ultrasonic transmitter and receiver channels, further having a control circuit for the control of these channels, the control circuit comprising:
   a memory including a plurality of addressable locations, each location of the plurality holding a plurality of different numbers which include time count numbers for the beginning and end of gating signals, and amplitude limit or reference numbers;
   a controller for providing a sequence of test identification numbers, each number identifying a particular test involving a particular transmitter and receiver channel;
   means connected for accessing the memory locations of the plurality in response to the test identification number to obtain a read-out of content of the accessed memory location, the contents of different memory locations being read out in accordance with said sequence of test identification numbers;
   storage means connected for receiving and storing the content of the accessed memory location as read out therefrom, including for each test so identified the time count numbers and at least one amplitude limit or reference number, the storage means receiving a new content for each test;
   a time counter means operating to count clock pulses;
   gating signal generator means including comparator means, and connected to receive the time count numbers from the means for receiving and storing and further connected to the counter for comparing the count numbers with the running time counts as counted by the time counter to generate gating signals in response thereto, the gating signals establishing looking windows;
   means connected to the controller for selecting and operating the particular transmitter channel in response to the test identification numbers to cause the channel to launch an ultrasonic test signal into a test object so that a sequence of tests is conducted in accordance with the sequence of test identification numbers as provided by the controller and wherein different test identification numbers involve different transmitter and receiver channels as selected, each test including the launching of a test signal by the transmitter in the selected channel;
   means connected to the receiver channels to receive therefrom a train of measuring signals, including particularly measuring signals following the operation of the selected transmitter channel, the measuring signals representing interaction of the test signal launched by the selected transmitter with the test object, further connected to be responsive to the gating signals to suppress measuring signals in the selected receiver channel outside of the gating signals and looking windows;
   comparing means connected to be response to the limit number as held in the means for receiving and storing, and to compare the limit number with the amplitude of a particular signal portion that occurred in one of the windows to determine occurrence of an amplitude in the signal portion, corresponding to the reference number;
   means for determining the time of said occurrence and providing a representation thereof as a measuring result; and
   processing means for updating said numbers as held in the several locations of the memory on the basis of measuring signals as occurring in particular ones of the said windows.

2. A system as in claim 1, the gating signal generator means including first and second independently operating gating signal generators, each receiving separately time count numbers from the means for receiving and storing;
   the first generator providing gating signals to the comparing means as a sequence of looking windows, the comparing means comparing the amplitude of the measuring signals in the windows of the sequence of windows with amplitude reference signals taken from the means for storing and receiving separately for each of the latter windows;
   amplitude detection means connected to receive the measuring signals;
   the second generator providing gating signals as a second sequence of windows to the amplitude detection means to detect the time of occurrence of a particular characteristics in the measuring signal separately for each window of the second sequence of windows.

3. In a system as in claim 1 and including means for tracking the number of windows being generated and causing the time count numbers in the means for receiving and storing to be updated under the same test identification number so that a plurality of sequential windows is being generated.

4. The system as in claim 2, wherein a pair of windows of the second sequence defines two periods of time in which echo signals from boundaries of the test object are to occur; and the detector means being connected to the time counter for marking the instants of occurrences of these echoes in the two windows.

5. A system as in claim 1, further including means connected to be responsive to the measuring signals for detecting the peak amplitude of the digital signals during a particular window period and means for marking the instants of occurrences of the peak amplitudes, and separately from the determination of the time of occurrence of an amplitude corresponding to said limit.

6. The system as in claim 1, including adjustable means responsive to external control signals for delaying responsiveness and selection of a receive channel on the basis of the test identification number; and external control means connected to provide said control signals to the adjustable means.

7. A system as in claim 1, wherein the locations include time count pre-set numbers and means to feed the respective pre-set number when held in the means for receiving and storing, to the time count means for presetting the counter means to define a particular time count starting point.

8. A system as in claim 1, the means for determining the time of occurrence being connected to the time counter means to identify the time count as concurring in particular instants of occurrence of the amplitude in the measuring signal corresponding to the reference value; and means for accumulating representation of the identified time counts under the current test identification number.

9. A system as in claim 1, including a source for electrical signals constituting externally furnished parameters, one of the parameters being signals defining a delay period being fed to and being received by the means for operating to determine the time of launching the test signal.

10. A system as in claim 9, said source connected to said controller to provide thereto signals determining the sequencing of the selection in response thereto.

11. A system as in claim 9 and including means for controlling the timing of responsiveness of a receiver channel as selected, the means for controlling being connected to receive electrical signals from the source to set the timing in response thereto.

12. A system as in claim 1, wherein the numbers held in said memory and received and stored by the storage means include transit time limit numbers; the system including further comparing means connected for comparing the time of said occurrence with a transit time limit as stored and providing a representation of the comparision.

13. A system as in claim 1, the controller including a counter to provide a regular sequence of said identification numbers, the controller further including means for changing said sequence.

14. In a system for inspecting test objects by means of ultrasonics, having a plurality of transmitter and receiver channels for ultrasonic signals, comprising:

means for generating a sequence of test identification numbers;

first circuit means connected for selecting a transmitter channel and a receiver channel in accordance with the current test identification number for purposes of conducting a test, a change in the number changes the selection;

second circuit means for selectively controlling the time of triggering a selected transmitter channel to launch an ultrasonic test signal, and for selectively rendering the selected receiver channel responsive for receiving ultrasonic response signals as resulting from interaction of the test signal with the test object, the selective times of triggering and for rendering responsive being made by the second circuit means on the basis of a first pair of electrical signals constituting first variable parameters to be received by the second circuit means;

external circuit means connected to provide said first pair of signals;

third circuit means connected to the receiver channels and receiving therefrom a data stream in the sequence of selection of the several channels;

fourth circuit means for generating a plurality of looking windows, each window being defined by a pair of time count numbers the fourth means including means for being responsive to and adjusted by second signals representing particular time count numbers to generate gating signals representing and defining those windows;

fifth circuit means connected to the third and fourth circuit means to search for specific, different characteristics in the data stream during the windows and on the basis of and in response to reference signals constituting third parameters and which are different for the different windows;

sixth circuit means including a memory addressable on the basis by the test identification numbers for furnishing the second signals to the fourth means as the time count numbers for the generation of the windows, and furnishing the reference signals to the fifths means as the third parameters, the second and the reference signals being provided in steps and individually for each test; and processing means responsive to the resulting data of the data stream as searched by the fifths means to recalculate the count numbers and/or reference parameters for use in a subsequent test.

15. In a system for ultrasonic inspection of test objects which includes a plurality of individually triggerable and enableable ultrasonic transmitter channels and ultrasonic receiver channel, the receiver channels having a common output channel providing a train of received signals, the improvement comprising:

control means for stepwise selecting a transmitter channel and a receiver channel of the channels to conduct a sequence of tests, each test including the launching of an ultrasonic test pulse into a test object, signals representing interaction of the test pulse with the test object being received by the selected receiver channel and passed to the common output channel;

first circuit means for generating at least one looking window in timed relations to a particular starting point, the timed relation being defined by electrical signals serving as operating parameters and being received by the first circuit means for setting the first circuit means;

second circuit means connected to the first circuit means and the common output channel for determining the occurrence of at least one particular level for an amplitude of the measuring signal as received and as occurring during said window, said occurrence being determined on the basis of a limit defined by an electrical signal also serving as an operating parameter and being received by the second circuit means for setting the second circuit means; and external control means for providing said electrical signals as said operating parameters to the first and second circuit means separately and individually to thereby set said first and second circuit means anew for each of said test steps.

16. A system as in claim 15, said control means operating in response to a predetermined delay for the launching of the test pulse, the delay being determined by a control parameter, the control means being provided to receive electrical signals representing the control parameter from said external control means thereby setting said delay.

17. A system as in claim 15, and including third circuit means for determining the time of that occurrence as a measuring result.

18. In a system as in claim 15, wherein the second circuit means includes means for comparing the time of occurrence with a time limit, the time limit being set by particular signals, said external control means also furnishing the signals setting the time limit.

19. A system as in claim 15, wherein the second circuit means includes means (a) for determining the occurrence of a plurality of amplitudes within particular limits, each said limits being separate parameters furnished by the external means.

20. A system as in claim 15, wherein said external control means includes a memory storing said operating parameters from the memory, and means for extracting said parameters sequentially for the sequence of tests.

21. In a system as in claim 15, and including means connected to the second circuit means for accumulating the result of the determination, and additional means connected to the last mentioned means for updating certain ones of the parameters as provided by the external control means.

22. In a system as in claim 16:
said control means for the selecting of a transmitter channel and of a receiver channel for the conduction of a test including means responsive to externally provided selection signals to change the selection in accordance with said selection signals constituting a first control parameter;
said control means further including means for controlling the duration of a test period in accordance with second signals constituting a second control parameter; and
means for selectively generating and updating the signals of and defining at least some of the parameters for said tests.

23. In a system as in claim 22, wherein said external control means includes a memory storing said operating parameters, and means connected to the control means for operating the memory to extract therefrom the operating parameters for the test conducted by the transmitter and receiver channels, as selected by the control means, said external control means additionally including source means for providing the signals constituting said first and second control parameters.

24. In a system for inspecting test objects by means of ultrasonic radiation and having a plurality of individually enablable and triggerable ultrasonic transmitter and receiver channels and for processing the signals of the receiver channels, further having a control and data acquisition circuit for the control of these channels, the control and acquisition circuit comprising:

a memory including a plurality of addressable locations, each location holding a plurality of digital control and operating parameters for the evaluation of ultrasonic receiver signals and including for each test as conducted by one of the channels a plurality of timing signals for the generation of looking windows; and at least one amplitude reference value:

a controller for providing a sequence of test identification numbers, each number identifying a particular test;

means connected to the controller for accessing the memory locations of the plurality in response to the test identification number to obtain a read out of the content of the accessed location, the contents of different memory locations being read out in accordance with said sequence of the test identification numbers;

storage means connected for receiving and temporarily storing the control and operating parameters of the read out locations, so that a different set of operating parameters is available for each of the tests as sequentially conducted by operation of said controller;

means connected to the controller for selecting and operating a particular transmitter channel in response to each of the test identification numbers as sequentially provided to cause the channel to launch an ultrasonic test signal for each of the tests;

first signal processing means connected to the receiver channels to receive therefrom a train of measuring signals, and for processing the measuring signals in accordance with the operating and control parameters as held in the means for receiving and storing, and including means for generating a plurality of looking windows for restricting inspection of the measuring signal to selected periods, the operating and control parameters include control signals for the timing of the looking windows, the first signal processing means generating a plurality of test data;

means for accumulating the test data under the test identification number for further processing; and further processing means connected for operating on the test data for calculating a new set of operating and control parameters and for updating the content of the memory location under the current test identification number for use in the next test as identified by said number.

25. A system as in claim 24 wherein the means for receiving and processing the measuring signals includes logarithmic, high frequency amplifier.

26. The system as in claim 24 wherein the means for receiving a train of signals includes a digitizer, the processing and generating being carried out digitally.

27. A system as in claim 26 wherein said digitizer includes means for adjusting the characteristics of the signal as received, one of the parameters being a digital corrective value used for the correction.

28. A system as in claim 24, the operating parameters as stored in the memory and as received by the storage means including amplitude reference values being updated in the storage means for each test, the first signal processing means including means responsive to an amplitude reference value as stored in the means for receiving and storing processing, for comparing the amplitude reference value as held in the means for receiving and storing with the measuring signals.

* * * * *